United States Patent [19]

Ohtsubo et al.

[11] Patent Number: 5,178,872
[45] Date of Patent: Jan. 12, 1993

[54] PESTICIDAL COMPOSITION CONTAINING A MICROENCAPSULATED ORGANO-PHOSPHORUS OR CARBAMATE IN A PYRETHROID DISPERSION

[75] Inventors: Toshiro Ohtsubo, Sanda; Shigenori Tsuda, Kyoto; Kozo Tsuji, Nara, all of Japan

[73] Assignee: Sumitomo Chemical Co., Ltd., Osaka, Japan

[21] Appl. No.: 610,678

[22] Filed: Nov. 8, 1990

[30] Foreign Application Priority Data

Nov. 10, 1989 [JP] Japan .................... 1-293395

[51] Int. Cl.⁵ .............................. A01N 25/28
[52] U.S. Cl. ...................... 424/408; 424/405; 514/65; 514/73; 514/963
[58] Field of Search .............. 424/408, 405; 514/65, 514/73, 963

[56] References Cited

U.S. PATENT DOCUMENTS

| | | | |
|---|---|---|---|
| 4,469,675 | 9/1984 | Curtis et al. | 424/78 |
| 4,557,755 | 12/1985 | Takahashi et al. | 71/100 |
| 4,889,719 | 12/1989 | Ohtsubo et al. | 424/408 |
| 4,900,551 | 2/1990 | Ohtsubo et al. | 424/408 |
| 4,938,797 | 7/1990 | Hässlin et al. | 71/118 |
| 4,956,129 | 9/1990 | Scher et al. | 264/4.7 |
| 4,970,031 | 11/1990 | Gotoh | 264/4.3 |

FOREIGN PATENT DOCUMENTS

| | | |
|---|---|---|
| 0008207 | 2/1980 | European Pat. Off. |
| 0238184 | 9/1987 | European Pat. Off. |
| 0368285 | 5/1990 | European Pat. Off. |
| 9008468 | 8/1990 | PCT Int'l Appl. |
| 2027346 | 2/1980 | United Kingdom |
| 2224655 | 5/1990 | United Kingdom |

Primary Examiner—Thurman K. Page
Assistant Examiner—Robert H. Harrison
Attorney, Agent, or Firm—Sughrue, Mion, Zinn, Macpeak & Seas

[57] ABSTRACT

An insecticidal and/or acaricidal and/or nematicidal composition having a rapid efficacy and residual activity which comprises a mixture of a poorly water-soluble organophosphorus insecticide and/or acaricide and/or nematicide and/or a poorly water-soluble carbamate insecticide and/or acaricide which have been microencapsulated in water-insoluble polymer coatings with a dispersing agent used in forming a microcapsule part, with a poorly water-soluble pyrethroid insecticide and/or acaricide emulsified or suspended in water with the above-mentioned dispersing agent used in forming a flowable part.

4 Claims, No Drawings

PESTICIDAL COMPOSITION CONTAINING A MICROENCAPSULATED ORGANO-PHOSPHORUS OR CARBAMATE IN A PYRETHROID DISPERSION The present invention relates to an insecticidal and/or acaricidal and/or nematicidal composition having a rapid efficacy and residual activity.

Insecticides, acaricides and nematicides have so far been used after formulated into a variety of forms in order that when used in practice they may be easily handled by users and the efficacy of their active ingredients may be exhibited to the fullest extent. Typical examples of such forms of formulation include emulsifiable concentrates, wettable powders, dusts, oil formulations, suspension concentrates, concentrated emulsions and microcapsules.

Emulsifiable concentrates are widely used because they are relatively easy to prepare and can be easily used by dilution with water. However, since organic solvents are used therein, they have problems in points of toxicity, inflammability, etc. Further, in the case of active ingredients which are very poorly soluble in organic solvents, formulating them into emulsifiable concentrates has been virtually impossible.

On the other hand, wettable powders can be formulated even with active ingredients whose solubility to organic solvents is very poor and, since they ordinarily require no organic solvents, the problem of inflammability is also eliminated. However, since they are in the form of powder, scattering of powders may occur when they are formulated or diluted with water, leading to the risk of operators inhaling the powder.

Although flowable formulations (suspension concentrates and concentrated emulsions), microcapsules, etc. have been developed in recent years, they are not fully satisfactory from the viewpoint of exhibiting both a rapid efficacy and a residual activity at the same time.

The present inventors have made extensive study to solve the above-mentioned problems. As a result, it has been found that an insecticidal and/or acaricidal and/or nematicidal composition having both a rapid efficacy and a residual activity can be obtained by microencapsulating a poorly water-soluble organophosphorus insecticide and/or acaricide and/or nematicide and/or a poorly water-soluble carbamate insecticide and/or acaricide in minute water-insoluble polymer coatings to form so-called microcapsules, separately emulsifying or suspending in water a poorly water-soluble pyrethroid insecticide and/or acaricide to form a so-called flowable formulation, and then mixing the two in suitable proportions. The present invention has been accomplished on the basis of this finding.

Thus, according to the present invention, there is provided an insecticidal and/or acaricidal and/or nematicidal composition having a rapid efficacy and residual activity which comprises a mixture of a poorly water-soluble organophosphorus insecticide and/or acaricide and/or nematicide (hereinafter referred to as the present organophosphorus pesticide) and/or a poorly water-soluble carbamate insecticide and/or acaricide (hereinafter referred to as the present carbamate pesticide) which have been microencapsulated in water-insoluble polymer coatings with a dispersing agent used in forming a microcapsule part (hereinafter referred to as the microcapsule part), with a poorly water-soluble pyrethroid insecticide and/or acaricide (hereinafter referred to as the present pyrethroid pesticide) emulsified or suspended in water with the above-mentioned dispersing agent used in forming a flowable part (hereinafter referred to as the flowable part) (said composition being hereinafter referred to as the present composition).

An amount of the dispersing agent to be added is from 0.05 to 10% by weight of the microcapsule part and is from 0.05 to 10% by weight of the flowable part. Thus, the dispersing agent amount is totally from 0.1 to 20% by weight of the present composition.

The present organophosphorus pesticide, carbamate pesticide and pyrethroid pesticide respectively have a solubility in water of preferably not more than 1,000 ppm at room temperature (ca. 25° C.).

The polymer coating usable in the present invention is not particularly limited so long as it is insoluble in water, and may be properly selected depending on the individual method of microencapsulating the present organophosphorus pesticide and/or the present carbamate pesticide with polymer coatings. Examples thereof include those of synthetic polymers such as polyamides, polyurethanes, polyesters, polysulfonamides, polyureas, epoxy resins, polysulfonates, polycarbonates, and urea-formaldehyde resins; or gelatin, gum arabic, sodium alginate, etc.; each used alone or in a combination of two or more thereof and water-insolubilized. Particularly preferred among them are polyurethanes and polyureas.

The methods to be used for encapsulating the present organophosphorus pesticide and/or the present carbamate pesticide in the water-insoluble polymer coating may be conventional ones used for microencapsulation, including the interfacial polymerization method, the in situ method, the drying in liquid method, and the coacervation method. Particularly preferred among them are the interfacial polymerization method and the in situ method.

Examples of dispersing agent used in forming the microcapsule part include at least one of the following synthetic polymers: poly(vinyl alcohol), poly(vinyl pyrrolidone), polyoxyethylene, block copolymers of ethylene oxide with propylene oxide, polymers containing carboxyl groups or the derivatives thereof, and condensation products of naphthalenesulfonic acid or xylenesulfonic acid derivatives with formaldehyde or the salts thereof, and/or at least one of the following semi-synthetic polymers: sodium salt of carboxymethylcellulose, lignin sulfonic acid salt, methylcellulose, hydroxyethylcellulose, hydroxypropylcellulose and hydroxypropylmethylcellulose; and/or at least one of the following natural polymers: gum arabic and gelatin.

As examples of said "polymers containing carboxyl groups or the derivatives thereof", there may be mentioned polymers of unsaturated monocarboxylic acids such as acrylic acid and methacrylic acid, unsaturated dicarboxylic acids such as maleic acid, and the derivatives thereof (e.g., alkyl esters thereof); copolymers of these monomers with each other; copolymers of said unsaturated carboxylic acids with monomers copolymerizable therewith, such as styrene, isobutylene and vinyl acetate; further, the alkali metal salts of these polymers and copolymers; and the mixtures thereof. As more specific examples, mention may be made of maleic acid-styrene copolymer, maleic acid-isobutylene copolymer, maleic acid-acrylic acid copolymer, saponification products of methyl acrylate-vinyl acetate copolymer, and the alkali metal salts thereof. When the ability of the dispersing agent used is not sufficiently acceptable, known surface active agents described, for example, in Gosei Kaimenkasseizai (Synthetic Surface Active Agents), written by Hiroshi Horiguchi, may be added thereto to improve dispersibility.

Emulsifying or suspending the present pyrethroid pesticide in water may be performed by adding said pesticide or, if necessary, a mixture of said pesticide with a hydrophobic solvent, to an aqueous solution containing a dispersing agent to give an emulsion of fine droplets or a suspension of fine particles.

Examples of dispersing agents used in emulsifying or suspending the present pyrethroid pesticide, namely in forming the flowable part, are the same as those used in forming the microcapsule part mentioned above. When the ability of the dispersing agent used is not sufficiently acceptable, known surface active agents described, for example, in Gosei Kaimenkasseizai (Synthetic Surface Active Agents), written by Hiroshi Horiguchi, may be added thereto to improve emulsion or suspension dispersibility.

A convenient method for emulsifying or dispersing in water the present pyrethroid pesticide or a hydrophobic mixture of said pesticide with a hydrophobic solvent etc. into fine droplets or particles is, for example, the use of a dispersing machine such as a homogenizer, colloid mill and disperser when they are liquid and the use of a wet grinding machine such as a bead mill, sand mill and colloid mill when they are solid.

In forming each of the microcapsule part and the flowable part, and also in forming the present composition, in other words after the microcapsule part and the flowable part have been mixed, there may be added as occasion demands a thickener. For example, there may be used at least one of the following polymeric thickeners: xanthan gum, locust bean gum, guar gum, carrageenan, alginic acid and its salts, and tragacanth gum, and/or at least one of the following inorganic fine powders: aluminum magnesium silicate, bentonite and synthetic hydrated silicone dioxide.

An amount of the thickener to be added is from 0.1 to 10% by weight of the present composition.

Further, if necessary, there may be added synergists such as piperonyl butoxide, stabilizers such as BHT, preservatives such as formalin, antifreezing agents such as propylene glycol and ethylene glycol, and anticrystallization agent such as phenylxylylethane.

The mixing of the microcapsule part and the flowable part may be performed in various ways as described below. In one method, the microcapsule part and the flowable part are each separately prepared, then the two parts are mixed, and an aqueous solution comprising the above-mentioned thickener etc. is added thereto. In another method, to an aqueous solution containing a dispersing agent used in forming the microcapsule part and a dispersing agent used in forming the flowable part, (1) there is added a solution containing the present organophosphorus pesticide and/or the present carbamate pesticide and a film material forming agent (i.e., monomers etc.) for microcapsules (i.e., polymer coatings) and is stirred until turned into fine droplets, then, if necessary, a corresponding film material forming agent (i.e., monomers etc.) is added, subsequently the present pyrethroid pesticide or a hydrophobic mixture of the present pyrethroid pesticide with a hydrophobic solvent etc. is added to the slurry obtained above and stirred until turned into fine droplets, and the resulting mixture is subjected to such an operation of microencapsulation by interfacial polymerization as stirring with heating in the range of 40° to 80° C. for a period of 0.5 to 48 hours, or (2) there is added the present pyrethroid pesticide or a hydrophobic mixture of the present pyrethroid pesticide with a hydrophobic solvent etc. and is stirred until turned into fine droplets, then a solution containing the present organophosphorus pesticide and/or the present carbamate pesticide and a film material forming agent (i.e., monomers etc.) for microcapsules is added and stirred until turned into fine droplets, then, if necessary, a corresponding film material forming agent (i.e., monomers etc.) is added, and then the resulting mixture is subjected to such an operation of microencapsulation by interfacial polymerization as stirring with heating in the range of 40° to 80° C. for a period of 0.5 to 48 hours; and thereafter an aqueous solution comprising the thickener etc. mentioned above is added thereto. The aqueous solution comprising the thickener etc. may be added also in any proceeding steps, if necessary.

The mixing ratio of the microcapsule part of the present invention and the flowable part of the present invention varies depending on the kind of active ingredients, the kind of target pests, target crops, the time, method and place of application, weather conditions, etc. and is not specifically limited. It is, however, usually from 1500:1 to 10:90 by weight as an active ingredient.

In using the present composition, it is sprayed as it is or, as occasion demands, after being diluted with water.

A convenient method for said spraying is to use a spraying machine used for spraying conventional emulsificable concentrates and flowable formulations. The present composition may be used also for so-called aerial application.

Specific examples of the effective ingredients usable in the present invention are listed below.

The present organophosphorus pesticide

O,O-Dimethyl O-4-nitro-m-tolyl phosphorothioate (fenitrothion)
S-[1,2-Bis(ethoxycarbonyl)ethyl] O,O-dimethyl phosphorodithioate (marathion)
O,O-Dimethyl O-(2-isopropyl-6-methyl-4-pyrimidinyl) phosphorothioate (diazinon)
O-(3,5,6-Trichloro-2-pyridyl) O,O-diethyl phosphorothioate (chlorpyrifos)
O-(2,2-Dichlorovinyl) O,O-dimethyl phosphate (dichlorvos)
O,O-Dimethyl O-(3-methyl-4-methylthiophenyl) phosphorothioate (fenthion)
S-(tert-Butylthio)methyl O,O-dimethyl phosphorodithioate (terbfos)
O,O-Dimethyl O-1-(N-methoxyimino)ethyl phosphorothioate
2-Methoxy-4H-1,3,2-benzodioxaphosphorin 2-sulfide (salithion)

The present carbamate pesticide 2-sec-Butylphenyl N-methylcarbamate (BPMC)
3,4-Dimethylphenyl N-methylcarbamate (MPMC)
3-Methylphenyl N-methylcarbamate (MTMC)

The present pyrethroid pesticide (RS)-α-Cyano-3-phenoxybenzyl (RS)-2-(4-chlorophenyl)-3-methylbutyrate (fenvalerate)
(S)-α-Cyano-3-phenoxybenzyl (S)-2-(4-chlorophenyl)-3-methylbutyrate (esfenvalerate)

(RS)-α-Cyano-3-phenoxybenzyl 2,2,3,3-tetramethylcyclopropanecarboxylate (fenpropathrin)

3-Phenoxybenzyl (1R)-cis,trans chrysanthemate (d-phenothrin)

(RS)-α-Cyano-3-phenoxybenzyl (1R)-cis,transchrysanthemate (cyphenothrin)

3-Phenoxybenzyl (1RS)-cis,trans-3-(2,2-dichlorovinyl)-2,2-dimethylcyclopropanecarboxylate (permethrin)

α-Cyano-3-phenoxybenzyl (1R)-cis,trans-3-(2,2-dichlorovinyl)-2,2-dimethylcyclopropanecarboxylate (cypermethrin)

α-Cyano-3-phenoxybenzyl (1R)-cis,trans-3-(2,2-dibromovinyl)-2,2-dimethylcyclopropanecarboxylate (deltamethrin)

2-(4-Ethoxyphenyl)-2-methylpropyl 3-phenoxybenzyl ether (ethofenprox)

(S)-α-Cyano-3-phenoxybenzyl (1R,3S)-2,2-dimethyl-3-(1,2,2,2-tetrabromoethyl)cyclopropanecarboxylate (tralomethrin)

3,4,5,6-Tetrahydrophthalimidomethyl (1RS)-cis,trans-chrysanthemate (tetramethrin)

3,4,5,6-Tetrahydrophthalimidomethyl (1R)-cis,trans-chrysanthemate (d-tetramethrin)

(RS)-3-Allyl-2-methyl-4-oxocyclopent-2-enyl (1RS) cis,trans-chrysanthemate (allethrin)

(RS)-3-Allyl-2-methyl-4-oxocyclopent-2-enyl (1R)-cis,-trans-chrysanthemate (d-allethrin)

(S)-2-Methyl-4-oxo-3-(2-propynyl)cyclopent-2-enyl (1R)-cis,trans-chrysanthemate (prallethrin)

(RS)-1-Ethynyl-2-methyl-2-pentenyl (1R)-cis,trans-chrysanthemate (empenthrin)

5-Benzyl-3-furylmethyl (1RS)-cis,transchrysanthemate (resmethrin)

5-Benzyl-3-furylmethyl (1R)-cis,transchrysanthemate (d-resmethrin)

α-Cyano-3-phenoxybenzyl [1R,trans]-2,2-dimethyl-3-(2-chloro-2-trifluoromethylvinyl)cyclopropanecarboxylate (cyhalothrin)

α-Cyano-3-phenoxybenzyl 2-(2-chloro-4-trifluoromethylanilino)isovalerate (fluvalinate)

α-Cyano-3-phenoxybenzyl 1-(4-ethoxyphenyl)-2,2-dichlorocyclopropanecarboxylate (cycloprothrin)

αCyano-4-fluoro-3-phenoxybenzyl [1R,trans]-2,2-dimethyl-3-(2,2-dichlorovinyl)cyclopropanecarboxylate (cyfluthrin)

α-Cyano-3-phenoxybenzyl 2-(4-difluoromethoxyphenyl)isovalerate (flucythrinate)

2-Methyl-3-phenylbenzyl [1R,trans]-2,2-dimethyl-3-(2-chloro-2-trifluoromethylvinyl)cyclopropanecarboxylate (bifenthrin)

2,3,5,6-Tetrafluoro-4-methylbenzyl [1R,trans]-2,2-dimethyl-3-(2-chloro-2-trifluoromethylvinyl)cyclopropanecarboxylate (tefluthrin) etc.

The present composition is effective against following pests, namely insect pests, acarine pests and soil nematodes in the fields of agriculture, forest and epidemic prevention which include Isoptera such as Formosan subterranean termite (*Coptotermes formosanus*) and *Reticulitermes speratus;* Dictyoptera such as German cockroach (*Blattella germanica*), smokybrown cockroach (*Periplaneta fuliginosa*) and American cockroach (*Periplaneta americana*); Lepidoptera such as tobacco cutworm (*Spodoptera litura*), diamondback moth (*Plutella xylostella*), common cabbage worm (*Pieris repaecrucivora*), rice leafroller (*Cnaphalocrocis medinalis*), rice armyworm (*Pseudaletia separate*), pink borer (*Sesamia inferens*), rice stem borer (*Chilo suppressalis*), beet armyworm (*Spodoptera exiqua*) and cabbage armyworm (*Mamesrta brassicae*); Hemiptera including planthoppers (Delphacidae), such as brown planthopper (*Nilaparvata lugens*), white-backed rice planthopper (*Sogatella furcifera*) and smaller brown planthopper (*Laodelphax striatellus*), leafhoppers (Deltocephalidae) such as green rice leafhopper (*Nephotettix cincticeps*), bugs, whiteflies (Aleyrodidae) such as greenhouse whitefly (*Trialeurodes voporariorum*), and aphids (Aphididae); Coleoptera including *Henosepilachna* such as twenty-eight-spotted ladybird (*Henosepilachna vigintioctopunctana*), powder post beatles (Lyctidae), longicorn beetles (Cerambycidae), weevils (Curculionidae), scarabs (Scarabaeidae) and Chrysomelidae such as corn root worms; Hymenoptera including ants (Formicidae), hornets (Vespidae), bethylid wasps (Bethylidae) and sawflies (Tenthridinidae) such as cabbage sawflies (*Athalia rosae ruficornis*); Orthoptera including mole crickets (Gryllotalpidae) and grasshoppers (Acrididae); soil nematodes such as root-lesion nematodes, cyst nematodes and root-knot nematodes; spider mites (Tetranychidae); ticks (Lxodidae); and, further, insect pests of Diptera including Culex species, Aedes species, Anopheles species, chironomid midges (Chironomidae), houseflies (Muscidae), blow flies (Calliphoridae), flesh flies (Sarcophagidae), anthomyiid flies (Anthomyiidae), fruit flies (Tephritidae), black flies (Simuliidae), tabanid flies (Tabanidae), and stable flies (Stomoxyidae).

EXAMPLES

The present invention will appear more fully from the Examples, Comparative Examples and Test Examples which follow.

EXAMPLE 1

To 200 g of fenitrothion was added 3.5 g of an addition product of toluene diisocyanate with trimethylolpropane (Sumidur L, a registered trade name, manufactured by Sumitomo-Bayer Urethane K.K.), and the mixture was stirred to form a uniform solution. The solution was added to 350 g of an aqueous solution containing 5% by weight of gum arabic as a dispersing agent, and stirred at room temperature (ca. 25° C.) for several minutes by using a T.K. Auto-homomixer (a trade name, manufactured by Tokushukika Kogyo K.K.) at a rotational speed of 5,600 rpm until turned into fine droplets. Then, 6 g of ethylene glycol was added to the mixture thus obtained and the resulting mixture was allowed to react with gentle stirring at 60° C. for 24 hours, whereby a slurry (A) containing fenitrothion microcapsules coated with polyurethane film was obtained.

Separately, 40 g of fenpropathrin was added to 80 g of phenylxylylethane, and the mixture was stirred to form a uniform solution. The solution was added to 350 g of an aqueous solution containing 5% by weight of gum arabic as a dispersing agent, and stirred at normal temperature for several minutes by using a T.K. Auto-homomixer (the same as described above) at a rotational speed of 7,000 rpm until turned into fine droplets, whereby a slurry (B) containing fenpropathrin was obtained.

Then, 559.5 g of the slurry (A) and 470 g of the slurry (B) were mixed with an aqueous solution containing 0.4% by weight of xanthan gum and 0.8% by weight of aluminum magnesium silicate as a thickener to give a total weight of 2,000 g, whereby the present composition (1) containing 10% by weight of fenitrothion and 2% by weight of fenpropathrin was obtained.

COMPARATIVE EXAMPLE 1

To 200 g of fenitrothion was added 3.5 g of an addition product of toluene diisocyanate with trimethylolpropane (the same as described above) and the mixture was stirred to form a uniform solution. The solution was added to 350 g of an aqueous solution containing 5% by weight of gum arabic as a dispersing agent, and stirred at room temperature for several minutes by using a T.K. Auto-homomixer (the same as described above) at a rotational speed of 5,600 rpm until turned into fine droplets. Then, 6 g of ethylene glycol was added to the mixture thus obtained and the resulting mixture was allowed to react with gentle stirring for 24 hours at 60° C., whereby a slurry containing fenitrothion microcapsules coated with polyurethane film was obtained.

Then, 559.5 g of the slurry was mixed with an aqueous solution containing 0.4% by weight of xanthan gum and 0.8% by weight of aluminum magnesium silicate as a thickener to give a total weight of 2,000 g, whereby a comparative composition (1) containing 10% by weight of fenitrothion was obtained.

COMPARATIVE EXAMPLE 2

To 80 g of phenylxylylethane was added 40 g of fenpropathrin and the mixture was stirred to form a uniform solution. The solution was added to 350 g of an aqueous solution containing 5% by weight of gum arabic as a dispersing agent, and stirred at room temperature for several minutes by using a T.K. Autohomomixer (the same as described above) at a rotational speed of 7,000 rpm until turned into fine droplets to obtain a dispersion containing fenpropathrin. Then, 470 g of the dispersion was mixed with an aqueous solution containing 0.4% by weight of xanthan gum and 0.8% by weight of aluminum magnesium silicate as a thickener to give a total weight of 2,000 g, whereby a comparative composition (2) containing 2% by weight of fenpropathrin was obtained.

EXAMPLE 2

To 200 g of fenitrothion was added 1.5 g of an addition product of toluene diisocyanate with trimethylolpropane (the same as described above) and the mixture was stirred to form a uniform solution. The solution was added to 350 g of an aqueous solution containing 5% by weight of gum arabic as a dispersing agent, and stirred at room temperature for several minutes by using a T.K. Auto-homomixer (the same as described above) at a rotational speed of 5,600 rpm until turned into fine droplets. Then, 6 g of ethylene glycol was added to the mixture thus obtained, and the resulting mixture was allowed to react with gentle stirring for 24 hours at 60° C., whereby a slurry (C) containing fenitrothion microcapsules coated with polyurethane film was obtained.

Separately, 200 g of fenpropathrin was added to 200 g of phenylxylylethane and the mixture was stirred to form a uniform solution. The solution was then added to 500 g of an aqueous solution containing 5% by weight of gum arabic as a dispersing agent, and stirred at room temperature for several minutes by using a T.K. Autohomomixer (the same as described above) at a rotational speed of 8,000 rpm until turned into fine droplets, whereby a slurry (D) containing fenpropathrin was obtained.

Then, 557.5 g of the slurry (C) and 900 g of the slurry (D) were mixed with an aqueous solution containing 0.4% by weight of xanthan gum and 0.8% by weight of aluminum magnesium silicate as a thickener to give a total weight of 2,000 g, whereby the present composition (2) containing 10% by weight of fenitrothion and 10% by weight of fenpropathrin was obtained.

COMPARATIVE EXAMPLE 3

To 200 g of fenitrothion was added 1.5 g of an addition product of toluene diisocyanate with trimethylolpropane (the same as described above) and the mixture was stirred to form a uniform solution. Then, the solution was added to 350 g of an aqueous solution containing 5% by weight of gum arabic as a dispersing agent, and stirred at room temperature for several minutes by using a T.K. Auto-homomixer (the same as described above) at a rotational speed of 5,600 rpm until turned into fine droplets. Then, 6 g of ethylene glycol was added to the mixture thus obtained, and the resulting mixture was allowed to react with gentle stirring at 60° C. for 24 hours to obtain a slurry containing fenitrothion microcapsules coated with polyurethane film. Then, 557.5 g of the slurry was mixed with an aqueous solution containing 0.4% by weight of xanthan gum and 0.8% by weight of aluminum magnesium silicate as a thickener to give a total weight of 2,000 g, whereby a comparative composition (3) containing 10% by weight of fenitrothion was obtained.

COMPARATIVE EXAMPLE 4

To 200 g of phenylxylylethane was added 200 g of fenpropathrin and the mixture was stirred to form a uniform solution. The solution was added to 500 g of an aqueous solution containing 5% by weight of gum arabic as a dispersing agent, and stirred at room temperature for several minutes by using a T.K. Autohomomixer (the same as described above) at a rotational speed of 8,000 rpm until turned into fine droplets, to obtain a dispersion containing fenpropathrin. Then, 900 g of the dispersion was mixed with an aqueous solution containing 0.4% by weight of xanthan gum and 0.8% by weight of aluminum magnesium silicate as a thickener to give a total weight of 2,000 g, whereby a comparative composition (4) containing 10% by weight of fenpropathrin was obtained.

EXAMPLE 3

To 200 g of fenitrothion was added 11 g of an addition product of toluene diisocyanate with trimethylolpropane (the same as described above), and the mixture was stirred to form a uniform solution. Then, the solution was added to 350 g of an aqueous solution containing 5% by weight of gum arabic as a dispersing agent, and stirred at room temperature for several minutes by using a T.K. Auto-homomixer (the same as described above) until turned into fine droplets. Then, 6.2 g of ethylene glycol was added to the mixture thus obtained, and the resulting mixture was allowed to react with gentle stirring at 60° C. for 24 hours to obtain a slurry (E) of fenitrothion microcapsules coated with polyurethane film.

Separately, a uniform mixture of 2.5 g of tralomethrin and 6.4 g of SOLVESSO 100 (a trade name, aromatic hydrocarbons, manufactured by Exxon Chemical K.K.) was added to 191.1 g of an aqueous solution containing 5% by weight of gum arabic as a dispersing agent, and stirred at room temperature for several minutes by using a T.K. Auto-homomixer (the same as described above) at a rotational speed of 8,000 rpm until turned into fine droplets, whereby a slurry (F) containing tralomethrin was obtained.

Then, 567.2 g of the slurry (E) and 20 g of the slurry (F) was mixed with an aqueous solution containing 0.4% by weight of xanthan gum and 0.8% by weight of aluminum magnesium silicate as a thickener to give a total weight of 1,000 g, whereby the present composition (3) containing 20% by weight of fenitrothion and 0.025% by weight of tralomethrin was obtained.

COMPARATIVE EXAMPLE 5

To 200 g of fenitrothion was added 11 g of an addition product of toluene diisocyanate with trimethylolpropane (the same as described above) and the mixture was stirred to form a uniform solution. The solution was added to 350 g of an aqueous solution containing 5% by weight of gum arabic as a dispersing agent, and stirred at room temperature for several minutes by using a T.K. Auto-homomixer (the same as described above) at a rotational speed of 5,600 rpm until turned into fine droplets. Then, 6.2 g of ethylene glycol was added to the mixture obtained, and the resulting mixture was allowed to react with gentle stirring at 60° C. for 24 hours to obtain a slurry containing fenitrothion microcapsules coated with polyurethane film. Then, 567.2 g of the slurry was mixed with an aqueous solution containing 0.4% by weight of xanthan gum and 0.8% by weight of aluminum magnesium silicate as a thickener to give a total weight of 1,000 g, whereby a comparative composition (5) containing 20% by weight of fenitrothion was obtained.

COMPARATIVE EXAMPLE 6

A uniform mixture of 2.5 g of tralomethrin and 6.4 g of Solvesso 100 (the same as described above) was added to 191.1 g of an aqueous solution containing 5% by weight of gum arabic as a dispersing agent, and stirred at room temperature for several minutes by using a T.K. Auto-homomixer (the same as described above) at a rotational speed of 8,000 rpm until turned into fine droplets, whereby a slurry containing tralomethrin was obtained. Then, 20 g of the slurry was mixed with an aqueous solution containing 0.4% by weight of xanthan gum and 0.8% by weight of aluminum magnesium silicate as a thickener to give a total weight of 1,000 g, whereby a comparative composition (6) containing 0.025% by weight of tralomethrin was obtained.

EXAMPLE 4

To 200 g of fenitrothion was added 11 g of an addition product of toluene diisocyanate with trimethylolpropane (the same as described above) and the mixture was stirred to form a uniform solution. The solution was added to 350 g of an aqueous solution containing 5% by weight of gum arabic as a dispersing agent, and stirred at room temperature for several minutes by using a T.K. Auto-homomixer (the same as described above) at a rotational speed of 5,600 rpm until turned into fine droplets. Then, 6.2 g of ethylene glycol was added to the mixture obtained and the resulting mixture was allowed to react with gentle stirring at 60° C. for 24 hours to obtain a slurry (G) containing fenitrothion microcapsules coated with polyurethane film.

Separately, a uniform mixture of 2.5 g of permethrin and 2.5 g of phenylxylylethane was added to 195 g of an aqueous solution containing 5% by weight of gum arabic as a dispersing agent, and stirred at normal temperature for several minutes by using a T.K. Auto-homomixer (the same as described above) at a rotational speed of 8,000 rpm until turned into fine droplets, whereby a slurry containing permethrin (H) was obtained.

Then, 567.2 g of the slurry (G) and 100 g of the slurry (H) were mixed with an aqueous solution containing 0.4% by weight of xanthan gum and 0.8% by weight of aluminum magnesium silicate as a thickener to give a total weight of 1,000 g, whereby the present composition (4) containing 20% by weight of fenitrothion and 0.125% by weight of permethrin was obtained.

COMPARATIVE EXAMPLE 7

A uniform mixture of 2.5 g of permethrin and 2.5 g of phenylxylylethane was added to 195 g of an aqueous solution containing 5% by weight of gum arabic as a dispersing agent, and stirred at room temperature for several minutes by using a T.K. Auto-homomixer (the same as described above) at a rotational speed of 8,000 rpm until turned into fine droplets, to obtain a slurry containing permethrin. Then, 100 g of the slurry was mixed with an aqueous solution containing 0.4% by weight of xanthan gum and 0.8% by weight of aluminum magnesium silicate as a thickener to give a total weight of 1,000 g, whereby a comparative composition (7) containing 0.125% by weight of permethrin was obtained.

EXAMPLE 5

To 200 g of fenitrothion was added 11 g of an addition product of toluene diisocyanate with trimethylolpropane (the same as described above) and the mixture was stirred to form a uniform solution. The solution was added to 350 g of an aqueous solution containing 5% by weight of gum arabic as a dispersing agent, and stirred at room temperature for several minutes by using a T.K. Auto-homomixer (the same as described above) at a rotational speed of 5,600 rpm until turned into fine droplets. Then, 6.2 g of ethylene glycol was added to the mixture obtained, and the resulting mixture was allowed to react with gentle stirring at 60° C. for 24 hours, whereby a slurry (I) containing fenitrothion microcapsules coated with polyurethane film was obtained.

Separately, a uniform mixture of 50 g of cyphenothrin and 50 g of phenylxylylethane was added to 350 g of an aqueous solution containing 5% by weight of gum arabic as a dispersing agent, and stirred at room temperature for several minutes by using a T.K. Auto-homomixer (the same as described above) at a rotational speed of 8,000 rpm until turned int fine droplets, whereby a slurry (J) containing cyphenothrin was obtained.

Then, 567.2 g of the slurry (I) and 450 g of the slurry (J) were mixed with an aqueous solution containing 0.6% by weight of xanthan gum and 1.2% by weight of aluminium magnesium silicate as a thickener to give a total weight of 2,000 g, whereby the present composition (5) containing 10% by weight of fenitrothion and 2.5% by weight of cyphenothrin was obtained.

COMPARATIVE EXAMPLE 8

A uniform mixture of 50 g of cyphenothrin and 50 g of phenylxylylethane was added to 350 g of an aqueous solution containing 5% by weight of gum arabic as a dispersing agent, and stirred at room temperature for several minutes by using a T.K. Auto-homomixer (the same as described above) at a rotational speed of 8,000 rpm until turned into fine droplets, whereby a slurry containing cyphenothrin was obtained. Then, 450 g of the slurry was mixed with an aqueous solution containing 0.6% by weight of xanthan gum and 1.2% by weight of aluminum magnesium silicate as a thickener to give a total weight of 2,000 g, whereby a comparative composition (8) containing 2.5% by weight of cyphenothrin was obtained.

COMPARATIVE EXAMPLE 9

To 200 g of fenitrothion was added 11 g of an addition product of toluene diisocyanate with trimethylolpropane (the same as described above) and the mixture was stirred to form a uniform solution. The solution was added to 350 g of an aqueous solution containing 5% by weight of gum arabic as a dispersing agent, and stirred at room temperature for several minutes by using a T.K. Auto-homomixer (the same as described above) at a rotational speed of 5,600 rpm until turned into fine droplets. Then, 6.2 g of ethylene glycol was added to the mixture obtained and the resulting mixture was allowed to react with gentle stirring at 60° C. for 24 hours, whereby a slurry of fenitrothion microcapsules coated with polyurethane film was obtained. Then, 567.2 g of the slurry was mixed with an aqueous solution containing 0.6% by weight of xanthan gum and 1.2% by weight of aluminum magnesium silicate as a thickener to give a total weight of 2,000 g, whereby a comparative composition (9) containing 10% by weight of fenitrothion was obtained.

EXAMPLE 6

The same procedures as in Example 5 were followed except for using esfenvalerate in place of cyphenothrin, to obtain the present composition (6) containing 10% by weight of fenitrothion and 2.5% by weight of esfenvalerate.

EXAMPLE 7

The same procedures as in Example 6 were followed except for using 100 g of d-phenothrin in place of 50 g of esfenvalerate and 50 g of phenylxylylethane, to obtain the present composition (7) containing 10% by weight of fenitrothion and 5% by weight of d-phenothrin.

EXAMPLE 8

The same procedures as in Example 1 were followed except for using cyphenothrin in place of fenpropathrin, to obtain the present composition (8) containing 10% by weight of fenitrothion and 2% by weight of cyphenothrin.

EXAMPLE 9

To 200 g of marathion was added 6 g of a self-condensation product of hexamethylene diisocyanate (Sumidur N, a registered trade name, manufactured by Sumitomo-Bayer Urethane K.K.) and the mixture was stirred to form a uniform solution. The solution was added to 350 g of an aqueous solution containing 10% by weight of poly(vinyl alcohol) as a dispersing agent, and stirred at room temperature for several minutes by using a T.K. Auto-homomixer (the same as described above) at a rotational speed of 4,000 rpm until turned into fine droplets. The mixture thus obtained was then allowed to react with gentle stirring at 60° C. for 24 hours, whereby a slurry (K) of marathion microcapsules coated with polyurea film was obtained.

Separately, 40 g of cypermethrin was added to 40 g of phenylxylylethane and the mixture was stirred to form a uniform solution. The solution was added to 350 g of an aqueous solution containing 10% by weight of polyvinyl alcohol as a dispersing agent, and stirred at room temperature for several minutes by using a T.K. Auto-homomixer (the same as described above) at a rotational speed of 7,000 rpm until turned into fine droplets, whereby a slurry (L) containing cypermethrin was obtained.

Then, 556 g of the slurry (K) and 430 g of the slurry (L) were mixed with an aqueous solution containing 0.4% by weight of xanthan gum and 0.8% by weight of aluminum magnesium silicate as a thickener to give a total weight of 2,000 g, whereby the present composition (9) containing 10% by weight of marathion and 2% by weight of cypermethrin was obtained.

EXAMPLE 10

To 200 g of fenitrothion was added 3.5 g of an addition product of toluene diisocyanate with trimethylolpropane (the same as described above) and the mixture was stirred to form a uniform solution. The solution was added to 700 g of an aqueous solution containing 5% by weight of gum arabic, and stirred at room temperature for several minutes by using a T.K. Auto-homomixer (the same as described above) at a rotational speed of 5,600 rpm until turned into fine droplets. A uniform mixture of 40 g of fenpropathrin and 80 g of phenylxylylethane was added to the slurry obtained above, and stirred for several minutes by using a T.K. Auto-homomixer (the same as described above) at a rotational speed of 7,000 rpm. Then, the resulting mixture was allowed to react with gentle stirring at 60° C. for 24 hours, and subsequently mixed with an aqueous solution containing 0.4% by weight of xanthan gum and 0.8% by weight of aluminum magnesium silicate as a thickener to give a total weight of 2,000 g, whereby the present composition (10) containing 10% by weight of fenitrothion and 2% by weight of fenpropathrin was obtained.

EXAMPLE 11

A uniform solution mixture of 40 g of fenpropathrin and 80 g of phenylxylylethane was added to 700 g of an aqueous solution containing 5% by weight of gum arabic as a dispersing agent, and stirred at room temperature for several minutes by using a T.K. Auto-homomixer (the same as described above) at a rotational speed of 7,000 rpm until turned into fine droplets. Then, a uniform solution of 3.5 g of an addition product of toluene diisocyanate with trimethylolpropane (the same as described above) in 200 g of fenitrothion was added to the slurry obtained above, and stirred at room temperature for several minutes by using a T.K. Auto-homomixer (the same as described above) at a rotational speed of 5,600 rpm until turned into fine droplets. Then, 6 g of ethylenediamine was added to the mixture obtained. The resulting mixture was allowed to react with gentle stirring at 60° C. for 24 hours, and then mixed with an aqueous solution containing 0.4% by weight of xanthan gum and 0.8% by weight of aluminum magnesium silicate as a thickener to give a total weight of 2,000 g, whereby the present composition (11) containing 10% by weight of fenitrothion coated with polyurea film and 2% by weight of fenpropathrin was obtained.

EXAMPLE 12

The same procedures as in Example 1 were followed except for using BPMC in place of fenitrothion, to obtain the present composition (12) containing 10% by weight of BPMC and 2% by weight of fenpropathrin.

EXAMPLE 13

The same procedures as in Example 1 were followed except for using a mixture of 150 g of fenitrothion and 50 g of BPMC in place of 200 g of fenitrothion, to obtain the present composition (13) containing 7.5% by weight of fenitrothion, 2.5% by weight of BPMC and 2% by weight of fenpropathrin.

TEST EXAMPLE 1

The present composition (1), comparative composition (1) and comparative composition (2) were each diluted 400-fold with a 5000-fold aqueous dilution of TOKUSEI RINO (a trade name, polyoxyethylenenoyl phenylether with calcium lignosulfonate, manufactured by Nippon Noyaku K.K.) and the diluted compositions were each applied to a cabbage planted in a pot at a rate of 20 ml per pot by means of a spray gun. After air-dried, one leaf was cut off from the cabbage, then placed in a cup 9 cm in diameter together with 10 tobacco cutworms, and immediately the behavior of the worms was observed and the mortality was determined. The results obtained are shown in Table 1.

Separately, one leaf each of a pesticide-treated cabbage was cut out every predetermined number of days after the treatment, then placed in a cup 9 cm in diameter together with 10 tobacco cutworms, and the percentage of dead and moribund worms after two days was examined. The results obtained are shown in Table 2.

TABLE 1

| Test formulation | Mortality (%) | | | |
|---|---|---|---|---|
| | 2 Hours after treatment | 3 Hours after treatment | 4 Hours after treatment | 5 Hours after treatment |
| Present composition (1) | 25 | 70 | 85 | 95 |
| Comparative composition (1) | 0 | 0 | 0 | 0 |
| Comparative composition (2) | 20 | 35 | 60 | 60 |
| No treatment | 0 | 0 | 0 | 0 |

TABLE 2

| Test formulation | Percentage of dead and moribund worms (%) | | |
|---|---|---|---|
| | 3 Days after treatment | 6 Days after treatment | 14 Days after treatment |
| Present composition (1) | 100 | 100 | 100 |
| Comparative composition (1) | 100 | 100 | 90 |
| Comparative composition (2) | 100 | 100 | 60 |
| No treatment | 0 | 0 | 0 |

TEST EXAMPLE 2

The present composition (2), comparative composition (3) and comparative composition (4) were each diluted 4000-fold with a 5000-fold aqueous dilution of Tokusei Rino (the same as described above), and the diluted compositions were each applied to a rice plant planted in a pot at a rate of 30 ml per 2 pots by means of a spray gun. After air-dried, one leaf was cut out from the rice plant, then placed in a cup 9 cm in diameter together with 10 brown planthoppers, and immediately the number of moribund insects was examined. Simultaneously, the mortality after 48 hours was also determined. The results obtained are shown in Tables 3 and 4.

TABLE 3

| Test formulation | Percentage of moribund insects (%) | | |
|---|---|---|---|
| | 1 Hour after treatment | 2 Hours after treatment | 13 Hours after treatment |
| Present composition (2) | 50 | 42 | 96 |
| Comparative composition (3) | 0 | 0 | 26 |
| Comparative composition (4) | 4 | 13 | 46 |

TABLE 4

| Test formulation | Mortality after 48 hours (%) |
|---|---|
| Present composition (2) | 96 |
| Comparative composition (3) | 65 |
| Comparative composition (4) | 46 |

TEST EXAMPLE 3

A sheet of filter paper was laid on the bottom of a Petri dish 9 cm in diameter, and 50 worker of Formosan subterranean termite were put in the dish. Then, 6 ml of a 12.5-fold aqueous dilution of the present composition (3) was sprayed from a height 60 cm above the dish. Immediately thereafter, 20 of the treated termites were transferred into a Petri dish 9 cmin diameter whose bottom had been covered with wet filter paper, to examine the number of moribund termites and to determine the time ($KT_{50}$) at which half of the termites became moribund.

The same tests as that for the present composition (3) were made also with comparative compositions (5) and (6). The results of these tests are shown in Table 5.

TABLE 5

| Test formulation | $KT_{50}$ (minutes) |
|---|---|
| Present composition (3) | 11 |
| Comparative composition (5) | 42 |
| Comparative composition (6) | 11 |

TEST EXAMPLE 4

In a Petri dish 9 cm in diameter was placed 10 g of soil moistened with water, and 6 ml of a 200-fold diluted liquid of the present composition (3) was sprayed from a height of 60 cm above the dish. Then, 20 worker of Formosan subterranean termite were put in the dish and the mortality 24 hours after the treatment was determined. Similar tests were made also with the present composition (4) and the comparative compositions (5), (6) and (7). The results thus obtained are shown in Table 6.

TABLE 6

| Test formulation | Mortality (%) |
|---|---|
| Present composition (3) | 93 |

TABLE 6-continued

| Test formulation | Mortality (%) |
|---|---|
| Present composition (4) | 90 |
| Comparative composition (5) | 20 |
| Comparative composition (6) | 55 |
| Comparative composition (7) | 3 |

TEST EXAMPLE 5

A 40-fold aqueous dilution of the present composition (5) was applied onto the surface of a plywood panel (15 cm × 15 cm) by means of a spray gun from a height 60 cm above the board so as to give an application rate of 50 ml/m$^2$, and then air-dried for 24 hours. Then, German cockroach adults (5 each males and females) were confined to contact with the treated surface for 2 hours to observe knock down effect. The test cockroaches were recovered after 2 hours and fed with diet and water to examine the mortality after 70 hours. Similar tests were made also with the comparative compositions (8) and (9). Comparison of the results thus obtained revealed that the present composition (5) exhibited excellent knock down effect and residual efficacy as compared with the comparative compositions (8) and (9).

COMPARATIVE EXAMPLE 10

A slurry (A) containing fenitrothion microcapsules coated with polyurethane film was obtained in the same manner as described in Example 1. Separately, 40 g of fenpropathrin was added to 80 of phenylxylylethane, and the mixture was stirred to form a uniform solution. The solution was added to 350 g of an aqueous solution containing 5% by weight of polyoxyethylene (20) sorbitan trioleate as a dispersing agent, and stirred at room temperature for several minutes by using a T.K. Autohomomixer (the same as described above) at a rotational speed of 7,000 rpm until turned into fine droplets, whereby a slurry (M) containing fenpropathrin was obtained.

Then, 559.5 g of the slurry (A) and 470 g of the slurry (M) were mixed with water to give a total weight of 2,000 g, whereby a comparative composition (10) containing 10% by weight of fenitrothion and 2% by weight of fenpropathrin was obtained.

COMPARATIVE EXAMPLE 11

A slurry (A) containing fenitrothion microcapsules coated with polyurethane film was obtained in the same manner as described in Example 1. Separately, an emulsifiable concentrate (A) containing 8% by weight of fenpropathrin was prepared by mixing 40 g of fenpropathrin, 50 g. of SORPOL 3005X (a registered trade name, a mixture of polyoxyethylene stylyl phenylether, its polymer and alkylarylsulfonate, mfd, by Toho Kagaku K.K) and 410 g of xylene.

Then, 559.5 g of the slurry (A) and 500 g of the emulsifiable concentrate (A) containing 8% by weight of fenpropathrin were mixed with water to give a total weight of 2,000 g, whereby a comparative composition (11) containing 10% by weight of fenitrothion and 2% by weight of fenpropathrin was obtained.

COMPARATIVE EXAMPLE 12

A slurry (A) containing fenitrothion microcapsules coated with polyurethane film was obtained in the same manner as described in Example 1. Separately, 40 g of fenpropathrin was added to 80 g of phenylxylylethane to form a uniform solution. The solution was mixed with 20 g of SORPOL 5060 (a registered trade name, alkylarylsulfonate with synthesized hydrated silicon dioxide, mfd by Toho Kagaku K.K), 10 g of DEMOR SNB (a registered trade name, sodium naphthalenesulfonate-formaldehyde condensate, mfd. by Kao K.K.), 100 g of synthetic hydrated silicone dioxide and 250 g of diatomaceous earth by means of a juice mixer, whereby a wettable powder (A) containing 8% by weight of fenpropathrin was obtained.

Then, 559.5 g of the slurry (A) and 500 g of the wettable powder (A) containing 8% by weight of fenpropathrin were mixed with water to give a total weight of 2,000 g, whereby a comparative composition (12) containing 10% by weight of fenitrothion and 2 by weight of fenpropathrin was obtained.

TEST EXAMPLE 6

Eighty grams each of the present composition (1) and the comparative compositions (10), (11) and (12) were respectively sealed in a 100-ml glass ampoule and stored at room temperature.

The comparative compositions (10), (11) and (12) all showed separation and sedimentation of dispersed particles after one day of storage, whereas the present composition (1) were stable even after one month of storage, showing no separation nor sedimentation of dispersed particles.

What is claimed is:

1. A pesticide having a rapid efficacy and residual activity as at least one of an insecticide, acaricide and nematicide, which comprises a mixture of a microencapsulated part and a flowable part, wherein the microencapsulated part comprises:
   (i) a poorly water-soluble organophosphorus insecticide, acaricide or nematicide; or
   (ii) a poorly water-soluble carbamate insecticide or acaricide which have been microencapsulated in water-insoluble polymer coatings with a dispersing agent used in forming a microcapsule part, and wherein the flowable part comprises
   (iii) a poorly water-soluble pyrethroid insecticide or acaricide emulsified or suspended in water with the above-mentioned dispersing agent used in forming a flowable part,
   wherein the amount of the dispersing agent to be added is from 0.05 to 10% by weight of the microcapsule part and is from 0.05 to 10% by weight of the flowable part.

2. The composition of claim 1 which further comprises from 0.1 to 10% by weight based on the entire composition of a thickener added after said microcapsule part and said flowable part have been mixed.

3. The composition of claim 1, wherein the dispersing agent is a synthetic polymer selected from the group consisting of poly(vinyl alcohol), poly(vinyl pyrrolidone), polyoxyethylene, block copolymers of ethylene oxide with propylene oxide, polymers containing carboxyl groups or the derivatives thereof, and condensation products of naphthalenesulfonic acid or xylenesulfonic acid derivatives with formaldehyde or the salts thereof, a semi-synthetic polymer selected from the group consisting of sodium salts of carboxymethylcellulose, lignin sulfonic acid salt, methylcellulose, hydroxyethylcellulose, hydroxypropylcellulose and hydroxypropylmethylcellulose; and/or a natural polymer selected from the group consisting of gum arabic and gelatin.

4. The composition of claim 2 wherein the thickener is a polymeric thickener selected from the group consisting of xanthan gum, locust bean gum, guar gum, carrageenan, alginic acid and its salts, and tragacanth gum, or an inorganic fine powder selected from the group consisting of aluminum magnesium silicate, bentonite and synthetic hydrated silicone dioxide.

* * * * *